United States Patent [19]
Millauer et al.

[11] 3,963,768
[45] June 15, 1976

[54] PROCESS FOR THE PREPARATION OF THIOCARBAMIC ACID O-ESTERS

[75] Inventors: Hans Millauer, Eschborn, Taunus; Gerhard Edelmann, Kelkheim, Taunus, both of Germany

[73] Assignee: Hoechst Aktiengesellschaft, Frankfurt am Main, Germany

[22] Filed: Dec. 13, 1974

[21] Appl. No.: 532,412

[30] Foreign Application Priority Data
Dec. 22, 1973 Germany............................ 2364316

[52] U.S. Cl............................................. 260/455 A
[51] Int. Cl.²...................................... C07C 155/02
[58] Field of Search................................ 260/455 A

[56] References Cited
UNITED STATES PATENTS

| | | | |
|---|---|---|---|
| 2,723,989 | 11/1955 | Harman............................ | 260/455 A |
| 2,852,361 | 9/1958 | Lesslie............................. | 260/455 A |
| 3,012,053 | 12/1961 | Lesslie............................. | 260/455 A |
| 3,297,680 | 1/1967 | Hamm et al..................... | 260/455 A |

OTHER PUBLICATIONS
Houben–Weyl Text vol. 2 pp. 832–833 (1952).

*Primary Examiner*—Lewis Gotts
*Assistant Examiner*—D. R. Phillips
*Attorney, Agent, or Firm*—Connolly and Hutz

[57] ABSTRACT

Process for the preparation of thiocarbamic acid-O-esters of the general formula

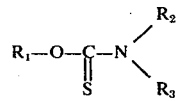

I in which $R_1$ means an alkyl or cycloalkyl radical, $R_2$ and $R_3$ each stands for an alkyl radical which may be substituted by one of the groups $-(O-C_2H_4)_n-OH$, $-(OC_2H_4)_n-OCH_3$ or $-O-(CH_2)_m-CH_3$, $n$ being 0, 1 or 2 and $m$ being 1 or 2, or stand for a cycloalkyl radical, and one of the radicals $R_2$ and $R_3$ may be hydrogen which process comprises reacting at a temperature ranging between 20° and 120°C in an aqueous or water-containing medium a xanthogenate of the formula

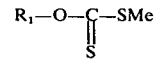

II in which $R_1$ is defined as above and Me is an alkali metal with a primary or secondary aliphatic amine of the formula

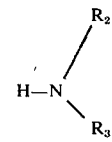

III in which $R_2$ and $R_3$ are defined as above, and elementary sulfur.

5 Claims, No Drawings

PROCESS FOR THE PREPARATION OF THIOCARBAMIC ACID O-ESTERS

The present invention relates to a process for the preparation of thiocarbamic acid O-esters. According to this invention the thiocarbamic acid O-esters are prepared by reacting salts of the dithiocarbonic acid-O-esters (xanthogenates) with primary or secondary aliphatic amines in the presence of elementary sulfur.

Thiocarbamic acid —O—esters have a wide-spread field of application in industry as collector in the flotation of sulfidic ores. (cf. U.S. Pat. Nos. 1,674,166 and 2,691,635).

Thiocarbamic acid-O-esters wich are also called thiourethanes, are known to be prepared according to various chemical processes (cf. Houben-Weyl, Methoden der organischen Chemie, 4th edition, vol. IX, pages 831–833, 1955).

A general method for their preparation is the reaction of dithiocarbonic acid-O,S-diesters in aqueous or alcoholic solution with primary or secondary amines:

R—O—C(S)—S—R' + HNR''R''' ⟶ R—O—C(S)—NR''R''' + R'—SH

A further general preparation method is the reaction of monothiocarbonic acid-O-ester-chlorides with the corresponding amines:

R—O—C—(S)—Cl + HNR''R''' ⟶ R—O—C(S)—NR''R''' + HCl

N-monosubstituted thiocarbamic acid-O-esters can also be prepared by addition reaction of alcohols or phenols with thioisocyanates (mustard oils):

R'—N=C=S + R—OH ⟶ R'—NH—C(S)—OR

In the formulae illustrated above R, R', R'' and ''' are alkyl radicals and R''' is also hydrogen.

All these known methods have, however, the drawback, that the preparation is relatively complicated and to be performed in several stages, for the starting substances are not so easily accesible but must be prepared from technically easily accessible sulfur compounds, for example the xanthogenates, in a separate chemical process. For example, dithiocarbonic acid-O,S-diesters are mainly obtained by the reaction of xanthogenates with organic halogen compounds, while monothiocarbonic acid-O-ester chlorides are obtained from thiophosgen and alcoholates or phenolates. An additional drawback of the preparational method via the dithiocarbonic acid-O,S-diesters is the formation of polluting mercaptanes as side products that must be neutralized by separate measures.

The present invention provides a new process for the preparation of thiocarbamic acid-O-esters in a single stage operation in which simple, easily accessible starting substances need not to be prepared any longer by complicated processes over several stages.

The present invention provides a process for the preparation of thiocarbamic acid-O-esters of the general formula

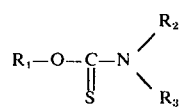

in which $R_1$ stands for a linear or branched alkyl radical of 1 to 8 carbon atoms, especially 2 to 4 carbon atoms, or a cycloalkyl radical of 4 to 6 carbon atoms and $R_2$ and $R_3$ independently from each other stand for a linear or branched alkyl radical of 1 to 6 carbon atoms, especially 2 to 4 carbon atoms which may also be substituted - preferably in β-position to the N-atom-by one of the groups —(O—CH$_2$—CH$_2$)$_n$ —OH, —(O—CH$_2$—CH$_2$)$_n$—O—CH$_3$ or —O—(CH$_2$)$_m$CH$_3$, ($n$ being 0, 1 or 2 and $m$ being 1 or 2), or a cycloalkyl radical of 4 to 6 carbon atoms and one of the radicals $R_2$ and $R_3$ also stands for hydrogen, which process comprises reacting a xanthogenate of the general formula

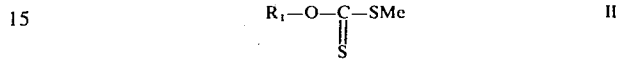

in which $R_1$ is defined as above and Me stands for an alkali metal, preferably potassium or sodium, in aqueos or water-containing medium with a primary or secondary aliphatic amine of the general formula

in which $R_2$ and $R_3$ are defined as above, and elementary sulfur at a temperature ranging from 20° to 120°C and separating and isolating the reaction product in known manner.

The xanthogenates indicated as starting substances are, in general, easily accessible by the reaction of carbon disulfide with the corresponding alcoholates according to the reaction equation

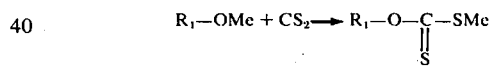

or they are available in commerce for the greatest part.

The process of the present invention can be performed, for example with the following xanthogenates:
 sodium methyl xanthogenate
 potassium ethyl xanthogenate
 potassium propyl xanthogenate
 sodium isopropyl xanthogenate
 potassium butyl xanthogenate
 potassium isobutyl xanthogenate
 sodium secondary butyl xanthogenate
 potassium amyl xanthogenate
 potassium hexyl xanthogenate
 potassium cyclohexyl xanthogenate
 potassium heptyl xanthogenate
 potassium octyl xanthogenate.

Suitable amines for the process of the invention are, for example, the following primary amines:
 methyl, ethyl, 2-hydroxyethyl, propyl, 2-hydroxypropyl, isopropyl, butyl, isobutyl, amyl, hexyl, cyclohexyl amine or the following secondary amines:
 dimethyl, diethyl, di-(2-hydroxy-ethyl), dipropyl, N-propyl-n-methyl-, N-isopropyl-N-methyl, N-cyclohexyl-N-methyl, N-propyl-N-ethyl, N-propyl-N-2-hydroxy-ethyl, N-sec.-butyl-N-ethyl, N-hexyl-N-ethyl amine.

The starting substances need not to be pure or fully homogeneous, for example commercial xanthogenates (xanthogenate content: 80–90% by w.) can be used, for, slight admixtures in the technical products, such as alkali metal hydroxide, alkali metal trithio carbonate, alkali metal thiosulfates or alkali metal carbonates do not hamper the process.

The quantitative ratio of the substances to be used for reaction is in general per mol of xanthogenate about 1.2 – 4.0 mols, preferably 2.0 – 3.5 mols of an amine of the formula III and about 1.2 to 5.0, preferably 1.5 to 4.0 gramme atoms of sulfur. The sulfur is preferably used in finely dispersed form.

The process of the invention is preferably performed in water as solvent or diluent which is generally used in an amount of at least 100 ml, preferably at least 150 ml, especially 200 to 400 ml per mol of the xanthogenate of the formula II. Higher amounts of water of for example 1000 ml per mol xanthogenate can be utilized, they are however not preferred. Additives of organic co-solvents, such as methanol, ethanol, isopropanol, dioxane, tetrahydrofurane can alleviate the process of the invention, especially when the starting substances are sparingly soluble in water.

The reaction temperatures are within the range of about 20° to 120°C. At room temperature, the reaction is very slow so that an at least moderately elevated temperature, over about 40°C, is useful to accelerate the reaction. Preferably, the reaction temperatures are 50° to 80°C.

The pressure essentially depends on the vapor pressure of the components in the reaction mixtures and is normally within a range of from atmospheric pressure to about 3 atmospheres gauge.

The reaction time is about 5 to 25 hours.

The process can be performed in known manner, for example by placing the starting substances with water and, optionally, other solvents in a heatable stirring vessel and heating to reaction temperature. The thiocarbamic acid-O-ester formed is mostly sparingly soluble in the reaction mixture, it can easily be separated and purified, for example by fractional distillation.

Thiocarbamic acid-O-esters, for example N-ethyl-thiocarbamic acid-O-isopropyl esters, are valuable products in industry and are significant as flotation auxiliaries for working up non ferrous metal ores.

The following Examples illustrate the invention, percentages are weight:

EXAMPLE 1

In a 1 liter stirring flask provided with thermometer and reflux cooler 175.5 g (1.0 mol) of sodium isopropyl xanthogenate (90%), 300 g (3.33 mols) of ethyl amine solution (aqueous, 50%), 120 g (3.75 mols) of sulfur (sublimated) and 200 g of water were placed. The mixture was heated to 55°C for 20 hours while stirring slowly. During that period of time, the solid substances were dissolved. At the same time, the N-ethyl-thiocarbamic acid-O-isopropyl ester was separated and the aqueous phase was covered.

After the reaction had been finished, the two phases were separated. The upper organic phase was freed from admixtures of ethyl amine in a rotary evaporator at 50°–60°C under 20–30 torr. The distillation residue obtained from this operation consisted in 95–98 % of N-ethyl-thiocarbamic acid-O-isopropyl ester (as per gas chromatography) and the amount was 138–141 g.

A further small amount of reaction product could be obtained by distilling the aqueous phase of the reaction mixture also under reduced pressure and isolating from the distillate (250–300 ml) by separation or extraction with methylene chloride and subsequent evaporation of the methylene chloride once more 2 – 3 g of N-ethyltiocarbamic acid-O-isopropyl ester.

The total yield was 141–143 g, that is 96–97 % of the theory, calculated on sodium isopropyl xanthogenate used.

EXAMPLE 2

182 g (1.0 mol) of potassium ethyl xanthogenate (88 %), 300 g (3.33 mols) of ethyl amine (aqueous, 50 %), 120 g (3.75 mols) of sulfur (sublimated) and 200 g of water were placed in a device as described in Example 1 and heated to 55°C for 24 hours while stirring.

The same procedure followed as has been described in Example 1.

114 g of N-ethyl-thiocarbamic acid-O-ethyl ester were obtained that corresponded to 86 % of the theory, calculated on xanthogenate used.

The degree of purity of the product evaluated by gas chromatography was 98.9 %.

EXAMPLE 3

232 g (1.0 mol) of potassium-n-hexyl-xanthogenate (94 %), 300 g (3.33 mols) of ethyl amine (aqueous, 50 %), 120 g (3.75 mols) of sulfur (sublimated) and 200 g of water were placed in a device as has been described in Example 1 and heated to 65°C for 24 hours while stirring.

The same procedure followed as has been described in Example 1, however, without distilling the aqueous phase or extracting the distillate.

188 g of N-ethyl-thiocarbamic acid-O-n-hexyl ester were obtained. As shown by gas chromatography, the degree of purity of the product was 84 %.

EXAMPLE 4

246 g (1.0 mol) of potassium-n-octyl xanthogenate, 300 g (3.33 mols) of ethyl amine (aqueous, 50 %), 120 g (3.75 mols) of sulfur (sublimated) and 200 g of water were placed in a device as has been described in Example 1 and heated to 65°C for 24 hours while stirring.

The same procedure followed as has been described in Example 3.

200 g of N-ethyl-thiocarbamic acid-O-n-octyl ester were obtained. As shown by gas chromatography, the degree of purity of the product was 81 %.

EXAMPLE 5

175.5 (1.0 mol) of sodium isopropyl xanthogenate (90 %), 233 g (3.0 mols) of methyl amine solution (aqueous, 40 %), 120 g (3.75 mols) of sulfur (sublimated) and 300 g of water were placed in a device as has been described in Example 1 and heated to 55°C for 24 hours while stirring.

The same procedure followed as has been described in Example 1.

124 g of N-methyl-thiocarbamic acid-O-isopropyl ester were obtained which corresponded to 93 % of the theory, calculated on xanthogenate used. As shown by gas chromatography, the degree of purity of the product was 99 %.

EXAMPLE 6

175.5 g (1.0 mol) of sodium isopropyl xanthogenate (90 %), 202 g (2.0 mols) of n-hexyl amine, 120 g (3.75 mols) of sulfur (sublimated), 200 g of methanol and 200 g of water were placed in a device as has been described in Example 1 and heated to 65°C for 24 hours while stirring.

After the reaction had been finished, the two phases were separated, the upper, organic phase was additioned with methylene chloride and then shaken with dilute sulfuric acid. The organic phase was separated once more and condensed at 70°–80°C under 25 torr.

The residue consisted of 190 g of N-n-hexyl-thiocarbamic acid-O-isopropyl ester. As shown by gas chromatography, the degree of purity of the product was 87 %.

EXAMPLE 7

175.5 g (1.0 mol) of sodium isopropyl xanthogenate (90 %), 219 g (3.0 mols) of diethyl amine, 120 g (3.75 mols) of sulfur (sublimated) and 400 g of water were placed in a device as has been described in Example 1 and heated to 55°C for 24 hours while stirring.

The same procedure followed as has been described in Example 3. 98 g of N-diethyl-thiocarbamic acid-O-isopropyl ester were obtained, that corresponded to 56 % of the theory, calculated on xanthogenate used. As shown by gas chromatography, the degree of purity of the product was 91 %.

EXAMPLE 8

175.5 g (1.0 mol) of sodium isopropyl xanthogenate (90 %), 204 g (3.33 mols) of ethanol amine, 120 g (3.75 mols) of sulfur (sublimated) and 400 g of water were placed in a device as has been described in Example 1 and heated to 55°C for 24 hours while stirring. The reaction mixture was worked up as has been described in Example 6.

112 g of N-(β-hydroxyethyl)-thiocarbamic acid-O-isopropyl ester were obtained which corresponded to 69 % of the theory, calculated on xanthogenate used. As shown by gas chromatography, the degree of purity of the product was 97 %.

What is claimed is:

1. Process for the preparation of thiocarbamic acid-O-esters of the formula

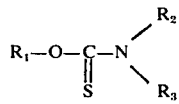   I in which $R_1$ stands for a linear or branched alkyl radical of 1 to 8 carbon atoms or a cycloalkyl radical of 4 to 6 carbon atoms, and $R_2$ and $R_3$ independently from each other stand for a linear or branched radical of 1 to 6 carbon atoms or such an alkyl radical is substituted by a group selected from $-(O-CH_2-CH_2)_n-OH$, $-(O-CH_2-CH_2)_n-O-CH_3$ and $-O-(CH_2)_m-CH_3$, $n$ being 0, 1 or 2 and $m$ being 1 or 2, or stand for cycloalkyl radical of 4 to 6 carbon atoms and one of the radicals $R_2$ and $R_3$ also stands for hydrogen, which process consists essentially of reacting at a temperature ranging between 20° and 120°C in an aqueous or water-containing medium 1 mol of a xanthogenate of the formula

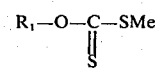   II in which $R_1$ is defined as above and Me is an alkali metal with a primary or secondary aliphatic amine of the formula

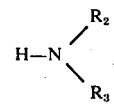   III in which $R_2$ and $R_3$ are defined as above, and 1.2 to 5 gram atoms of elementary sulfur.

2. Process as claimed in claim 1, wherein 1.2 to 4.0 mols of the amine of formula III are used.

3. Process as claimed in claim 1, wherein an alkali metal isopropyl xanthogenate is reacted with ethyl amine and sulfur.

4. Process as claimed in claim 1, wherein the reaction is carried out in at least 100 ml of water.

5. Process for the preparation of thiocarbamic acid-O-esters of the formula

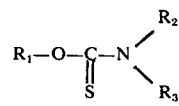   I as claimed in claim 1 in which formula $R_2$ and $R_3$ each stands for an alkyl radical of 1 to 6 carbon atoms which is substituted in β-position to the N-atom by a group selected from $-(O-CH_2-CH_2)_n-OH$, $-(O-CH_2-CH_2)_n-O-CH_3$ and $-O-(CH_2)_m-CH_3$, $n$ being 0, 1 or 2 and $m$ being 1 or 2.

* * * * *